(12) United States Patent
King

(10) Patent No.: US 11,900,185 B2
(45) Date of Patent: Feb. 13, 2024

(54) SYSTEMS AND METHODS FOR IMPROVING PERFORMANCE OF AN ANALOG PROCESSOR

(71) Applicant: D-WAVE SYSTEMS INC., Burnaby (CA)

(72) Inventor: Andrew Douglas King, Vancouver (CA)

(73) Assignee: 1372934 B.C. LTD., Burnaby (CA)

( * ) Notice: Subject to any disclaimer, the term of this patent is extended or adjusted under 35 U.S.C. 154(b) by 658 days.

(21) Appl. No.: 16/934,790

(22) Filed: Jul. 21, 2020

(65) Prior Publication Data

US 2020/0349326 A1 Nov. 5, 2020

Related U.S. Application Data

(63) Continuation of application No. PCT/US2019/014546, filed on Jan. 22, 2019.
(Continued)

(51) Int. Cl.
*G06J 1/00* (2006.01)
*G06N 10/00* (2022.01)
(Continued)

(52) U.S. Cl.
CPC .............. *G06J 1/00* (2013.01); *A61K 31/496* (2013.01); *A61K 45/06* (2013.01); *G06N 3/063* (2013.01);
(Continued)

(58) Field of Classification Search
None
See application file for complete search history.

(56) References Cited

U.S. PATENT DOCUMENTS 6,373,294 B1 4/2002 Bentley
6,911,664 B2 6/2005 Il et al.
(Continued)

FOREIGN PATENT DOCUMENTS

KR 101446943 B1 10/2014
WO 2005093649 A1 10/2005
(Continued)

OTHER PUBLICATIONS

Amin et al., "First Order Quantum Phase Transition in Adiabatic Quantum Computation", arXiv:0904.1387v3, Dec. 15, 2009, 5 pages.
(Continued)

*Primary Examiner* — Alan Chen
(74) *Attorney, Agent, or Firm* — Cozen O'Connor

(57) ABSTRACT

In a hybrid computing system including at least one analog processor and at least one digital processor an embedded problem is repeatedly run or executed on the analog processor(s) to generate a first plurality of candidate solutions to the computational problem, the candidate solutions are returned to the digital processor(s) which determine a value for at least one statistical feature of the candidate solutions, at least one programmable parameter of the plurality of analog devices in the analog processor(s) is adjusted to at least partially compensate for deviations from an expected value of the at least one statistical feature, the expected value of the at least one statistical feature inferred from the structure of the embedded problem, the embedded problem is again repeatedly run or executed on the analog processor(s) to generate a second plurality of candidate solutions to the computational problem.

22 Claims, 6 Drawing Sheets

Related U.S. Application Data

(60) Provisional application No. 62/620,282, filed on Jan. 22, 2018.

(51) Int. Cl.
*G06N 3/063* (2023.01)
*G06N 5/04* (2023.01)
*A61K 31/496* (2006.01)
*A61K 45/06* (2006.01)
*A61N 5/06* (2006.01)
*A61N 5/10* (2006.01)

(52) U.S. Cl.
CPC .............. *G06N 5/04* (2013.01); *G06N 10/00* (2019.01); *A61N 5/062* (2013.01); *A61N 5/10* (2013.01)

(56) References Cited

U.S. PATENT DOCUMENTS

| | | | |
|---|---|---|---|
| 7,135,701 B2 | 11/2006 | Amin et al. | |
| 7,230,266 B2 | 6/2007 | Hilton et al. | |
| 7,307,275 B2 | 12/2007 | Lidar et al. | |
| 7,418,283 B2 | 8/2008 | Amin | |
| 7,533,068 B2 | 5/2009 | Maassen et al. | |
| 7,619,437 B2 | 11/2009 | Thom et al. | |
| 7,639,035 B2 | 12/2009 | Berkley | |
| 7,843,209 B2 | 11/2010 | Berkley | |
| 7,876,248 B2 | 1/2011 | Berkley et al. | |
| 7,898,282 B2 | 3/2011 | Harris et al. | |
| 7,921,072 B2 | 4/2011 | Bohannon et al. | |
| 7,932,907 B2 | 4/2011 | Nachmanson et al. | |
| 7,984,012 B2 | 7/2011 | Coury et al. | |
| 8,008,942 B2 | 8/2011 | Van et al. | |
| 8,018,244 B2 | 9/2011 | Berkley | |
| 8,035,540 B2 | 10/2011 | Berkley et al. | |
| 8,098,179 B2 | 1/2012 | Bunyk et al. | |
| 8,169,231 B2 | 5/2012 | Berkley | |
| 8,174,305 B2 | 5/2012 | Harris | |
| 8,175,995 B2 | 5/2012 | Amin | |
| 8,190,548 B2 | 5/2012 | Choi | |
| 8,195,596 B2 | 6/2012 | Rose et al. | |
| 8,283,943 B2 | 10/2012 | Van Den Brink et al. | |
| 8,421,053 B2 | 4/2013 | Bunyk et al. | |
| 8,429,108 B2 | 4/2013 | Eusterbrock | |
| 8,560,282 B2 | 10/2013 | Love et al. | |
| 8,854,074 B2 | 10/2014 | Berkley | |
| 8,874,477 B2 | 10/2014 | Hoffberg | |
| 8,972,237 B2 | 3/2015 | Wecker | |
| 9,189,217 B2 | 11/2015 | Von Platen et al. | |
| 9,588,940 B2 | 3/2017 | Hamze et al. | |
| 9,710,758 B2 | 7/2017 | Bunyk et al. | |
| 10,031,887 B2 | 7/2018 | Raymond | |
| 10,650,050 B2 | 5/2020 | He et al. | |
| 10,872,021 B1 | 12/2020 | Tezak et al. | |
| 11,062,227 B2* | 7/2021 | Amin | B82Y 10/00 |
| 11,087,616 B2 | 8/2021 | Rom et al. | |
| 11,422,958 B2 | 8/2022 | Boothby et al. | |
| 2002/0180006 A1 | 12/2002 | Franz et al. | |
| 2002/0188578 A1 | 12/2002 | Amin et al. | |
| 2003/0102470 A1 | 6/2003 | Il et al. | |
| 2003/0169041 A1 | 9/2003 | Coury et al. | |
| 2005/0008050 A1 | 1/2005 | Fischer et al. | |
| 2007/0180586 A1 | 8/2007 | Amin | |
| 2007/0239366 A1 | 10/2007 | Hilton et al. | |
| 2008/0052055 A1 | 2/2008 | Rose et al. | |
| 2009/0078931 A1 | 3/2009 | Berkley | |
| 2009/0192041 A1 | 7/2009 | Johansson et al. | |
| 2009/0259905 A1 | 10/2009 | Silva et al. | |
| 2009/0261319 A1 | 10/2009 | Maekawa et al. | |
| 2009/0289638 A1 | 11/2009 | Farinelli et al. | |
| 2010/0150222 A1 | 6/2010 | Meyers et al. | |
| 2011/0054876 A1 | 3/2011 | Biamonte et al. | |
| 2011/0057169 A1 | 3/2011 | Harris et al. | |
| 2011/0060780 A1 | 3/2011 | Berkley et al. | |
| 2011/0065586 A1 | 3/2011 | Maibaum et al. | |
| 2011/0138344 A1 | 6/2011 | Ahn | |
| 2012/0023053 A1 | 1/2012 | Harris et al. | |
| 2012/0087867 A1 | 4/2012 | McCamey et al. | |
| 2012/0144159 A1 | 6/2012 | Pesetski et al. | |
| 2012/0265718 A1 | 10/2012 | Amin et al. | |
| 2013/0106476 A1 | 5/2013 | Joubert et al. | |
| 2013/0117200 A1 | 5/2013 | Thom | |
| 2013/0267032 A1 | 10/2013 | Tsai et al. | |
| 2014/0229722 A1 | 8/2014 | Harris | |
| 2015/0262073 A1 | 9/2015 | Lanting | |
| 2015/0286748 A1 | 10/2015 | Lilley | |
| 2015/0363708 A1 | 12/2015 | Amin et al. | |
| 2016/0079968 A1 | 3/2016 | Strand et al. | |
| 2016/0233860 A1 | 8/2016 | Naaman | |
| 2016/0238360 A1 | 8/2016 | Naud et al. | |
| 2016/0267032 A1 | 9/2016 | Rigetti et al. | |
| 2016/0364653 A1 | 12/2016 | Chow et al. | |
| 2017/0017894 A1 | 1/2017 | Lanting et al. | |
| 2017/0104695 A1 | 4/2017 | Naaman | |
| 2017/0300454 A1 | 10/2017 | Van Den Brink et al. | |
| 2017/0351967 A1* | 12/2017 | Babbush | G06N 20/00 |
| 2017/0364362 A1 | 12/2017 | Lidar et al. | |
| 2018/0101786 A1 | 4/2018 | Boothby | |
| 2018/0123544 A1 | 5/2018 | Abdo | |
| 2019/0019098 A1 | 1/2019 | Przybysz | |
| 2019/0042677 A1 | 2/2019 | Matsuura et al. | |
| 2019/0042967 A1 | 2/2019 | Yoscovits et al. | |
| 2019/0043919 A1 | 2/2019 | George et al. | |
| 2019/0266508 A1 | 8/2019 | Bunyk et al. | |
| 2019/0378874 A1 | 12/2019 | Rosenblatt et al. | |
| 2019/0391093 A1 | 12/2019 | Achlioptas et al. | |
| 2019/0392352 A1 | 12/2019 | Lampert et al. | |
| 2020/0005155 A1 | 1/2020 | Datta et al. | |
| 2020/0183768 A1 | 6/2020 | Berkley et al. | |
| 2020/0334563 A1 | 10/2020 | Gambetta et al. | |
| 2020/0342345 A1* | 10/2020 | Farhi | G06N 3/082 |
| 2020/0349326 A1 | 11/2020 | King | |
| 2020/0379768 A1 | 12/2020 | Berkley et al. | |
| 2020/0380396 A1 | 12/2020 | Raymond | |
| 2022/0207404 A1 | 6/2022 | Boothby | |

FOREIGN PATENT DOCUMENTS

| | | |
|---|---|---|
| WO | 2007085074 A1 | 8/2007 |
| WO | 2012064974 A2 | 5/2012 |
| WO | 2014123980 A1 | 8/2014 |
| WO | 2016-182608 A2 | 11/2016 |
| WO | 2016183213 A1 | 11/2016 |
| WO | 2017214331 A1 | 12/2017 |
| WO | 2018064535 A1 | 4/2018 |
| WO | 2018111242 A1 | 6/2018 |
| WO | 2019005206 A1 | 1/2019 |
| WO | 2019070935 A2 | 4/2019 |
| WO | 2019168721 A1 | 9/2019 |
| WO | 2020112185 A2 | 6/2020 |
| WO | 2021011412 A1 | 1/2021 |

OTHER PUBLICATIONS

Amin et al., Macroscopic Resonant Tunneling in the Presence of Low Frequency Noise, arXiv:0712.0845 [cond-mat.mes-hall], May 13, 2008, pp. 1-4.

Amin, "Effect of Local Minima on Adiabatic Quantum Optimization," Physical Review Letters 100(130503), 2008, 4 pages.

Aspuru-Guzik. "Simulated Quantum Computation of Molecular Energies", Science, Sep. 9, 2005.

Whittaker, J.D., et al., "A frequency and sensitivity tunable microresonator array for high-speed quantum," arXiv:1509.05811v2 [quant-ph], Apr. 22, 2016, 8 pages., Apr. 22, 2016.

Berkley, A.J. et al., "Tunneling Spectroscopy Using a Probe Qubit," arXiv:1210.6310v2 [cond-mat.supr-con], Jan. 3, 2013, 5 pages.

Bunyk et al., "Architectural Considerations in the Design of a Superconducting Quantum Annealing Processor," IEEE Trans. Appl. Supercond., 24, arXiv:1401.5504v1 [quant-ph] Jan. 21, 2014, 9 pages.

(56) References Cited

OTHER PUBLICATIONS

Byrd, "A Limited-Memory Algorithm for Bound-Contrained Optimization". SIAM Journal on Scientific Computing, Jun. 17, 2005.
Dhande et al. "End-User Calibration for Quantum Annealing". Engineering Project Report—UBC, Jan. 6, 2019.
D-Wave, "Technical Description of the D-Wave Quantum Processing Unit", D-Wave User Manual 09-1109A-M, Sep. 24, 2018, 56 pages.
Gao, Jiansong, "The Physics of Superconducting Microwave Resonators," Thesis, in Partial Fulfillment of the Requirements for the Degree of Doctor of Philosophy, California Institute of Technology Pasadena, California, May 28, 2008, 197 pages.
Harris et al., "Probing Noise in Flux Qubits via Macroscopic Resonant Tunneling", arXiv:0712.0838v2 [cond-mat.mes-hall], Feb. 8, 2008, pp. 1-4.
International Search Report for PCT/US2019/047747, dated Jun. 26, 2020, 4 pages.
King et al., "Observation of topological phenomena in a programmable lattice of 1,800 qubits", arXiv:1803.02047 [quant-ph], Mar. 6, 2018, 17 pages.
Lanting et al., "Geometrical dependence of the low-frequency noise in superconducting flux qubits", Physical Review B, 79, 060509, Jun. 5, 2009, 4 pages.
Lanting et al., "Probing High Frequency Noise with Macroscopic Resonant Tunneling", arXiv:1103.1931v1 [cond-mat.supr-con], Mar. 20, 2011, 5 pages.
Lanting, T., "Observation of Co-tunneling in Pairs of Coupled Flux Qubits", arXiv:1006.0028v1 [cond-mat.supr-con], May 31, 2010, 4 pages.
Manucharyan et al., "Fluxonium: single Cooper pair circuit free of charge offsets", arXiv:0906.0831v2, [cond-mat.mes-hall] Oct. 20, 2009, 13 pages.
Nielsen, "The Fermionic canonical commutation relations and the Jordan-Wigner transform", School of Physical Sciences, Jul. 29, 2005.
Petersan et al., "Measurement of resonant frequency and quality factor of microwave resonators: Comparison of methods," Journal of Applied Physics, vol. 84, No. 6, Sep. 15, 1998, 11 pages.
Sete et al., "A Functional Architecture for Scalable Quantum Computing", 2016 IEEE International Conference on Rebooting Computing (ICRC), Oct. 17, 2016, 5 pages.
Swenson et al., "Operation of a titanium nitride superconducting microresonator detector in the nonlinear regime," arXiv:1305.4281v1 [cond-mat.supr-con], May 18, 2013, 11 pages.
Yohannes et al, "Planarized, Extensible, Multilayer, Fabrication Process for Superconducting Electronics", IEEE Transactions on Applied Superconductivity, vol. 25, No. 3, Jun. 2015.
Tolpygo et al., "Advanced Fabrication Processes for Superconducting Very Large Scale Integrated Circuits," IEEE Transactions on Applied Superconductivity 26(3):1-10, Jan. 19, 2016.
Van Harlingen et al., "Decoherence in Josephson-junction qubits due to critical current fluctuations", arXiv:cond-mat/0404307v1 [cond-mat.supr-con], Apr. 13, 2004, 24 pages.
Written Opinion for PCT/US2019/047747, dated Jun. 26, 2020, 4 pages.
Boothby, K., "Input/Output Systems and Methods for Superconducting Devices," U.S. Appl. No. 62/860,098, filed Jun. 11, 2019, 31 pages.
Boothby, K., et al., "Systems and Methods for Efficient Input and Output to Quantum Processors," U.S. Appl. No. 62/851,377, filed May 22, 2019, 40 pages.
Chen, Y. et al., "Multiplexed Dispersive Readout of Superconducting Phase Qubits," Applied Physics Letters 101 (182601), 2012, 4 pages.
Heinsoo, J. et al., "Rapid high-fidelity multiplexed readout of superconducting qubits," arXiv:1801.07904v1 [quant-ph], Jan. 24, 2018, 13 pages.
International Search Report & Written Opinion for PCT/US2020/041703 dated Oct. 27, 2020, 9 pages.
International Search Report for PCT/US2020/037222, dated Sep. 17, 2020, 3 pages.
Michotte, S., "Qubit Dispersive Readout Scheme with a Microstrip Squid Amplifier," arXiv:0812.0220v1 [cond-mat.supr-con], Dec. 1, 2008, 4 pages.
Tolpygo et al., "Advanced Fabrication Process for Superconducting Very Large Scale Integrated Circuits", https://arxiv.org/abs/1509.05081, accessed Sep. 16, 2015.
Vollmer, R., "Fast and scalable readout for fault-tolerant quantum computing with superconducting Qubits," Master's Thesis, QuTech, Department of Quantum Nanoscience, Delft University of Technology, Jul. 10, 2018, 80 pages.
Written Opinion for PCT/US2020/037222, dated Sep. 17, 2020, 5 pages.
International Search Report and Written Opinion for PCT/US2019/014546, dated May 13, 2019, 9 pages.
Extended EP Search Report dated Jun. 26, 2023, EP App No. 20841331.0-11203—14 pages.
Notice of Allowance for U.S. Appl. No. 17/272,052, dated Aug. 3, 2023, 10 pages.
Harris et al., "Experimental Demonstration of a Robust and Scalable Flux Qubit," arXiv:0909.4321v1, Sep. 24, 2009, 20 pages.
Whiticar, et al., Probing flux and charge noise with macroscopic resonant tunneling, arXiv:2210.01714v1 [quant-ph] Oct. 4, 2022. 11 pages.

\* cited by examiner

SYSTEMS AND METHODS FOR IMPROVING PERFORMANCE OF AN ANALOG PROCESSOR

FIELD

This disclosure generally relates to analog processors such as quantum processors, and associated systems, devices, methods, and articles.

BACKGROUND

Quantum Devices

Quantum devices are structures in which quantum mechanical effects are observable. Quantum devices include circuits in which current transport is dominated by quantum mechanical effects. Such devices include spintronics, and superconducting circuits. Both spin and superconductivity are quantum mechanical phenomena. Quantum devices can be used for measurement instruments, in computing machinery, and the like.

Quantum Computation

A quantum computer is a system that makes direct use of at least one quantum-mechanical phenomenon, such as, superposition, tunneling, and entanglement, to perform operations on data. The elements of a quantum computer are qubits. Quantum computers can provide speedup for certain classes of computational problems such as computational problems simulating quantum physics.

Quantum Annealinq

Quantum annealing is a computational method that may be used to find a low-energy state of a system, typically preferably the ground state of the system. Similar in concept to classical simulated annealing, the method relies on the underlying principle that natural systems tend towards lower energy states because lower energy states are more stable. While classical annealing uses classical thermal fluctuations to guide a system to a low-energy state, quantum annealing may use quantum effects, such as quantum tunneling, as a source of delocalization to reach an energy minimum more accurately and/or more quickly than classical annealing.

A quantum processor may be designed to perform quantum annealing and/or adiabatic quantum computation. An evolution Hamiltonian can be constructed that is proportional to the sum of a first term proportional to a problem Hamiltonian and a second term proportional to a delocalization Hamiltonian, as follows:

$$H_E \propto A(t)H_P + B(t)H_D$$

where $H_E$ is the evolution Hamiltonian, $H_P$ is the problem Hamiltonian, $H_D$ is the delocalization Hamiltonian, and $A(t)$, $B(t)$ are coefficients that can control the rate of evolution, and typically lie in the range [0,1].

In some implementations, a time-varying envelope function can be placed on the problem Hamiltonian. A suitable delocalization Hamiltonian is given by:

$$H_D \propto -\frac{1}{2}\sum_{i=1}^{N} \Delta_i \sigma_i^x$$

where N represents the number of qubits, f is the Pauli x-matrix for the $i^{th}$ qubit and $\Delta_i$ is the single qubit tunnel splitting induced in the $i^{th}$ qubit. Here, the of terms are examples of "off-diagonal" terms.

A common problem Hamiltonian includes a first component proportional to diagonal single qubit terms and a second component proportional to diagonal multi-qubit terms, and may be of the following form:

$$H_P \propto -\frac{\varepsilon}{2}\left[\sum_{i=1}^{N} h_i \sigma_i^z + \sum_{j>i}^{N} J_{ij}\sigma_i^z\sigma_j^z\right]$$

where N represents the number of qubits, $\sigma_i^z$ is the Pauli z-matrix for the $i^{th}$ qubit, $h_i$ and $J_{ij}$ are dimensionless local fields for the qubits, and couplings between qubits, respectively, and $\varepsilon$ is some characteristic energy scale for $H_P$.

Here, the $\sigma_i^z$ and $\sigma_i^z\sigma_j^z$ terms are examples of diagonal terms. The former is a single-qubit term, and the latter a two-qubit term.

Throughout this specification, the terms "problem Hamiltonian" and "final Hamiltonian" are used interchangeably unless the context dictates otherwise. Certain states of the quantum processor are, energetically preferred, or simply preferred by the problem Hamiltonian. These include the ground states but may include excited states.

Hamiltonians such as $H_D$ and $H_P$ in the above two equations, respectively, may be physically realized in a variety of different ways. A particular example is realized by an implementation of superconducting qubits.

BRIEF SUMMARY

A method of operation of a hybrid computing system that comprises an analog processor and at least one digital processor, the analog processor and the at least one digital processor communicatively coupled to one another, the analog processor comprising a plurality of analog devices, the plurality of analog devices characterized by at least one programmable parameter, the at least one programmable parameter programmable by the digital processor, may be summarized as including: embedding, by the at least one digital processor, a computational problem on the analog processor to generate an embedded problem; causing, by the at least one digital processor, a first repeated running of the embedded problem on the analog processor to generate a first plurality of candidate solutions to the computational problem; returning to the at least one digital processor the first plurality of candidate solutions to the computational problem; determining, by the at least one digital processor, a value for at least one statistical feature of the first plurality of candidate solutions to the computational problem; adjusting the at least one programmable parameter of the plurality of analog devices in the analog processor to at least partially compensate for deviations from an expected value of the at least one statistical feature, the expected value of the at least one statistical feature inferred from the structure of the embedded problem; and causing, by the at least one digital processor, a second repeated running of the embedded problem on the analog processor to generate a second plurality of candidate solutions to the computational problem.

Embedding, by the at least one digital processor, a computational problem on the analog processor to generate an embedded problem may include embedding, by the at least one digital processor, a computational problem on a quantum processor. Embedding, by the at least one digital processor, a computational problem on a quantum processor may include embedding, by the at least one digital processor, a computational problem on a superconducting quantum processor.

Adjusting the at least one programmable parameter of the plurality of analog devices in the analog processor to at least partially compensate for deviations from an expected value of the at least one statistical feature may include adjusting the at least one programmable parameter of a plurality of superconducting flux qubits and superconducting coupling devices in the superconducting quantum processor. Adjusting the at least one programmable parameter of a plurality of superconducting flux qubits and superconducting coupling devices in the superconducting quantum processor may include adjusting at least one of a flux, a flux bias offset, a coupling strength and an anneal offset.

Embedding, by the at least one digital processor, a computational problem on the analog processor to generate an embedded problem may include embedding, by the at least one digital processor, an optimization problem on the analog processor.

Adjusting the at least one programmable parameter of the plurality of analog devices in the analog processor to at least partially compensate for deviations from an expected value of the at least one statistical feature, the expected value of the at least one statistical feature inferred from the structure of the embedded problem may include adjusting the at least one programmable parameter of the plurality of analog devices in the analog processor to at least partially compensate for deviations from an expected value of the at least one statistical feature, the expected value of the at least one statistical feature inferred from one or more symmetries of the embedded problem. Adjusting the at least one programmable parameter of the plurality of analog devices in the analog processor to at least partially compensate for deviations from an expected value of the at least one statistical feature, the expected value of the at least one statistical feature inferred from the structure of the embedded problem may include adjusting the at least one programmable parameter of the plurality of analog devices in the analog processor to at least partially compensate for deviations from an expected value of the at least one statistical feature, the expected value of the at least one statistical feature inferred from one or more graph automorphisms of the embedded problem.

Determining, by the at least one digital processor, a value for at least one statistical feature of the first plurality of candidate solutions to the computational problem may include determining, by the at least one digital processor, a value for at least one of a magnetization and a spin-spin correlation.

Embedding, by the at least one digital processor, a computational problem on the analog processor to generate an embedded problem may include embedding, by the at least one digital processor, a computational problem on a topology comprising a repeating lattice.

Embedding, by the at least one digital processor, a computational problem on a topology comprising a repeating lattice may include embedding, by the at least one digital processor, a computational problem on a topology comprising at least one of a triangular lattice and a square lattice.

The method of operation of the hybrid computing system may further include: returning to the at least one digital processor the second plurality of candidate solutions to the computational problem; determining, by the at least one digital processor, a value for at least one statistical feature of the second plurality of candidate solutions to the computational problem; and adjusting the at least one programmable parameter of the plurality of analog devices in the analog processor to at least partially compensate for deviations from the expected value of the at least one statistical feature.

A hybrid computing system may be summarized as including: at least one analog processor comprising a plurality of analog devices; at least one digital processor-based device communicatively coupled to the at least one analog processor; and at least one non-transitory computer-readable storage medium that stores processor-executable instructions, which when executed causes at least one processor-based device to: embed a computational problem on the analog processor to generate an embedded problem; cause by a first repeated running of the embedded problem on the analog processor to generate a first plurality of candidate solutions to the computational problem; return to the digital processor the first plurality of candidate solutions to the computational problem; determine a value for at least one statistical feature of the first plurality of candidate solutions to the computational problem; adjust the at least one programmable parameter of the plurality of analog devices in the analog processor to at least partially compensate for deviations from an expected value of the at least one statistical feature, the expected value of the at least one statistical feature inferred from the structure of the embedded problem; and cause a second repeated running of the embedded problem on the analog processor to generate a second plurality of candidate solutions to the computational problem.

The analog processor may include a quantum processor. The quantum processor may include a superconducting quantum processor.

The at least one programmable parameter of the plurality of analog devices may include at least one programmable parameter of a plurality of superconducting flux qubits and superconducting coupling devices in the superconducting quantum processor.

The processor-executable instructions, which when executed causes at least one processor-based device to adjust the at least one programmable parameter of a plurality of superconducting flux qubits and superconducting coupling devices in the superconducting quantum processor may include instructions, which when executed causes at least one processor-based device to adjust at least one of a flux, a flux bias offset, a coupling strength and an anneal offset.

The computational problem may include an optimization problem. The structure of the embedded problem may include one or more symmetries of the embedded problem. The structure of the embedded problem includes one or more graph automorphisms of the embedded problem.

The at least one statistical feature of the first plurality of candidate solutions may include at least one of a magnetization and a spin-spin correlation.

The analog processor may include a topology comprising a repeating lattice. In some implementations, the repeating lattice is at least one of a triangular lattice and a square lattice.

The hybrid computing system may further include at least one non-transitory computer-readable storage medium that stores processor-executable instructions, which when executed causes at least one processor-based device to: return to the digital processor the second plurality of candidate solutions to the computational problem; determine a value for at least one statistical feature of the second plurality of candidate solutions to the computational problem; and adjust the at least one programmable parameter of the plurality of analog devices in the analog processor to at least partially compensate for deviations from the expected value of the at least one statistical feature.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements are arbitrarily enlarged and positioned to improve drawing legibility. Further, the particular shapes of the elements as drawn are not necessarily intended to convey any information regarding the actual shape of the particular elements, and have been selected for ease of recognition in the drawings.

DETAILED DESCRIPTION

General Comments

Figure 1:
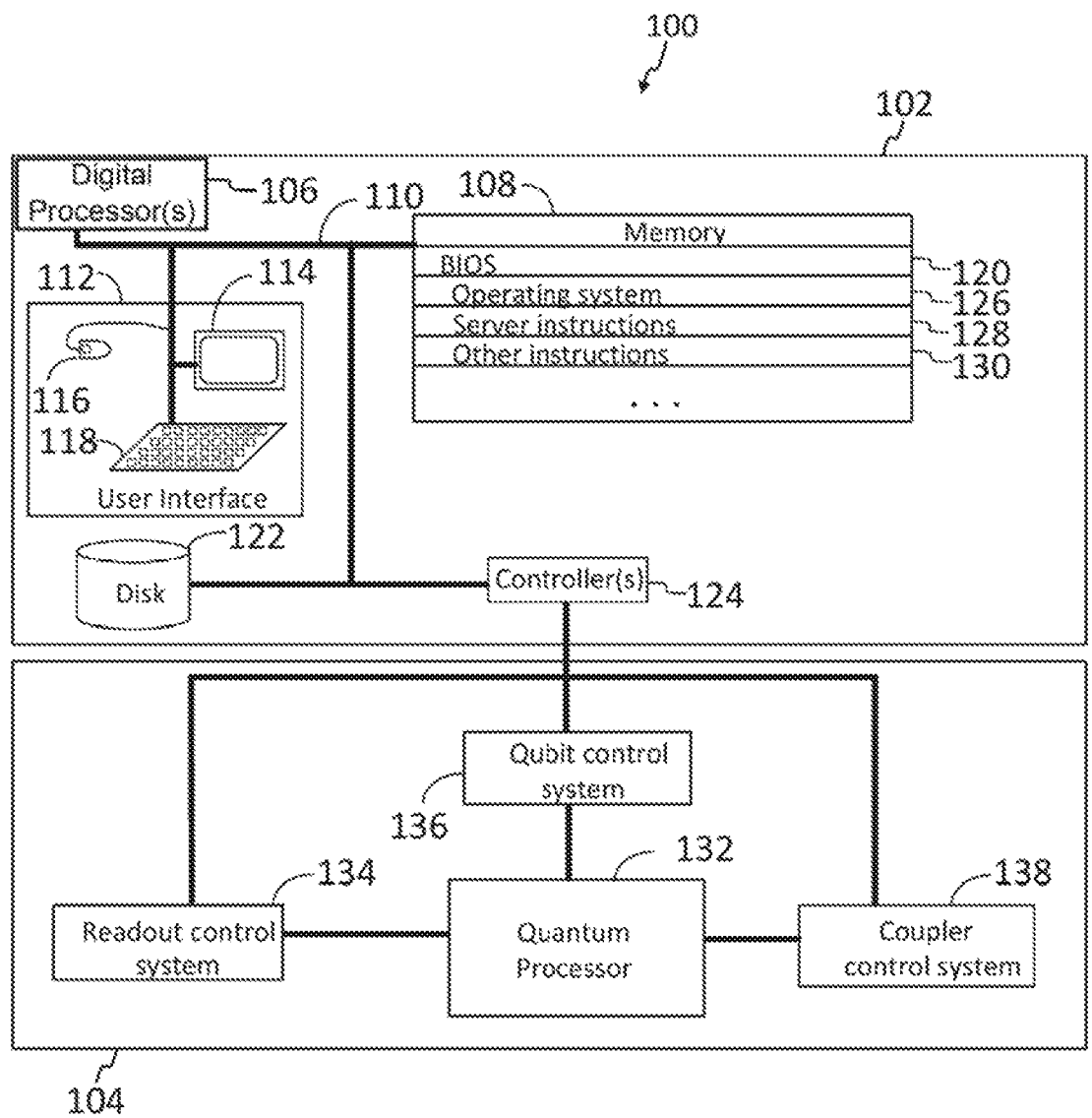
FIG. 1 is a schematic diagram of an example hybrid computing system including a digital computer coupled to an analog computer, in accordance with the present systems, devices, articles, and methods.

In the following description, some specific details are included to provide a thorough understanding of various disclosed embodiments. One skilled in the relevant art, however, will recognize that embodiments may be practiced without one or more of these specific details, or with other methods, components, materials, etc. In other instances, well-known structures associated with quantum processors, such as quantum devices, couplers, and control systems including microprocessors and drive circuitry have not been shown or described in detail to avoid unnecessarily obscuring descriptions of the embodiments of the present methods. Throughout this specification and the appended claims, the words "element" and "elements" are used to encompass, but are not limited to, all such structures, systems, and devices associated with quantum processors, as well as their related programmable parameters.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" "an embodiment", "another embodiment", "one example", "an example", "another example", "one implementation", "another implementation", or the like means that a particular referent feature, structure, or characteristic described in connection with the embodiment, example, or implementation is included in at least one embodiment, example, or implementation. Thus, the appearances of the phrases "in one embodiment", "in an embodiment", "another embodiment" or the like in various places throughout this specification are not necessarily all referring to the same embodiment, example, or implementation. Furthermore, the particular features, structures, or characteristics may be combined in any suitable manner in one or more embodiments, examples, or implementations.

It should be noted that, as used in this specification and the appended claims, the singular forms "a," "an," and "the" include plural referents unless the content clearly dictates otherwise. Thus, for example, reference to a problem-solving system including "a quantum processor" includes a single quantum processor, or two or more quantum processors. It should also be noted that the term "or" is generally employed in its sense including "and/or" unless the content clearly dictates otherwise.

The headings provided herein are for convenience only and do not interpret the scope or meaning of the embodiments.

Glossary

Automorphism: An automorphism of a graph is a form of symmetry in which the graph is mapped onto itself while preserving the edge-vertex connectivity. An automorphism of a graph $G=(V, E)$ (with a vertex set V and an edge set E) is a permutation $\sigma$ of V, such that a pair of vertices $(V_1, V_2)$ form an edge if and only if the pair $(\sigma(V_1), \sigma(V_2))$ also form an edge.

Chimera topology: A Chimera graph of size $C_s$ is an s×s grid of Chimera cells (also referred to in the present application as unit tiles or unit cells), each containing a complete bipartite graph on 8 vertices (a $K_{4,4}$ graph). Each vertex is connected to its four neighbors inside the cell as well as two neighbors (north/south or east/west) outside the cell. Every vertex has degree 6 excluding boundary vertices.

Edge-transitive graph: An edge-transitive graph is a graph G such that, given any pair of edges $(E_1, E_2)$, there is an automorphism of G that maps edge $E_1$ to edge $E_2$.

Frustration: A system is frustrated when the global ordering of the system is not compatible with the local ordering of its particles. In frustrated magnetic systems, for example, the localized magnetic moments, or spins, interact through competing exchange interactions that cannot be simultaneously satisfied. In the Ising model, for example, frustration means there is at least one $h_i$ or $J_{ij}$ that provides a positive contribution to the ground state energy, i.e., at least one satisfiability constraint on the $h_i$ and $J_{ij}$ values that is violated.

Superconducting Quantum Processor for Quantum Annealing

A superconducting quantum processor can be designed for quantum annealing (and/or adiabatic quantum computing—see below) components from which may be used to implement the present systems and methods. The superconducting quantum processor can comprise a plurality of superconducting qubits and at least one coupler providing a tunable $\sigma_i^z \sigma_j^z$ coupling (diagonal coupling) between qubits.

The quantum processor can include a plurality of interfaces that are used to configure and control the state of quantum processor. Each of interfaces can be realized by a respective inductive coupling structure, e.g., inductor, as part of a programming subsystem and/or an evolution subsystem.

In the operation of the quantum processor, interfaces can be used to couple a flux signal into a respective compound Josephson junction of the qubits, thereby realizing a tunable tunneling term (the $\Delta_i$ term) in the system Hamiltonian. This coupling provides the off-diagonal $\sigma^x$ terms of the Hamiltonian, and these flux signals are examples of "delocalization signals".

Similarly, interfaces can be used to apply a flux signal into a respective qubit loop of the qubits, thereby realizing the $h_i$ terms in the system Hamiltonian. This coupling provides the diagonal $\sigma^z$ terms in the system Hamiltonian. Furthermore, an interface can be used to couple a flux signal into a coupler, thereby realizing the $J_{ij}$ term(s) in the system Hamiltonian. This coupling provides the diagonal $\sigma_i^z \sigma_j^z$ terms in the system Hamiltonian.

The quantum processor can include readout devices to read out the final states of the qubits. Examples of superconducting qubits include superconducting flux qubits, superconducting charge qubits, and the like.

Adiabatic Quantum Computing

One model of quantum computing is adiabatic quantum computing. Adiabatic quantum computing can be suitable for solving hard optimization problems, for example. Adiabatic quantum computing may be considered a special case of quantum annealing. In adiabatic quantum computation, the system ideally begins and remains in its ground state throughout an adiabatic evolution. Those of skill in the art will appreciate that quantum annealing systems and methods may generally be implemented on an adiabatic quantum computer. Throughout this specification and the appended claims, any reference to quantum annealing is intended to encompass adiabatic quantum computation unless the context requires otherwise.

Calibration of Quantum Computers

Operation of a quantum computer such as a quantum annealer can include one or more calibration activities. See, for example, Perdomo-Ortiz A. et al., "Determination and correction of persistent biases in quantum annealers", Scientific Reports 6:18628 (2016) which describes adjustment of local fields (the $h_i$ terms in the system Hamiltonian) in the trivial instance of full symmetry and two-qubit systems. A shortcoming of existing systems and methods, such as the approach described by Ortiz, is that they are not applicable to non-trivial problems, and non-trivial symmetries of the problem, and are unable to correct for multi-body cross-talk, for example.

See also, for example US Patent Application Publication No. US2017/0017894 entitled "Systems and methods for improving the performance of a quantum processor to reduce intrinsic/control errors" which describes systems and methods for improving the performance of an analog processor such as a quantum processor by implementing a calibration correction for local bias values $h_i$ of qubits that belong to a logical qubit. The method can include determining whether the logical qubit exhibits a bias toward a basis state (e.g., a bias toward +1 or −1), and adjusting one or more local bias values to at least partially compensate for the bias exhibited by the logical qubit.

Hybrid Computing System Comprising a Quantum Processor

A hybrid computing system can include a digital computer communicatively coupled to an analog computer. In some implementations, the analog computer is a quantum computer and the digital computer is a classical computer.

The digital computer can include a digital processor that can be used to perform classical digital processing tasks described in the present systems and methods. The digital computer can include at least one system memory which can be used to store various sets of computer-readable or processor-readable instructions, application programs and/or data.

The quantum computer can include a quantum processor that includes programmable elements such as qubits, couplers, and other devices. The quantum computer can include a readout system, and the readout system can be operable to read out qubits, and communicate results to the digital computer. The quantum computer can include a qubit control system and a coupler control system. The qubit and the coupler control systems can control the qubits and the couplers, respectively. In some implementations, the qubit and the coupler control systems can be used to implement quantum annealing on the analog computer.

FIG. 1 illustrates an example hybrid computing system 100 including a digital computer 102 coupled to an analog computer 104. In some implementations, the analog computer 104 is a quantum computer and the digital computer 102 is a classical computer.

The exemplary digital computer 102 includes at least one digital processor 106, and each digital processor 106 may include one or more central processor units (not shown in FIG. 1). Only one digital processor 106 is shown in FIG. 1. Digital processor(s) 106 may be used to perform classical digital processing tasks described in the present systems and methods. In other implementations, digital computer 102 can include more than one digital processor. Those skilled in the relevant art will appreciate that the present systems and methods can be practiced with other digital computer configurations, including hand-held devices, multiprocessor systems, microprocessor-based or programmable consumer electronics, personal computers ("PCs"), network PCs, mini-computers, mainframe computers, and the like, when properly configured or programmed to form special purpose machines, and/or when communicatively coupled to control an analog computer, for instance a quantum computer.

Digital computer 102 will at times be referred to in the singular herein, but this is not intended to limit the application to a single digital computer. The present systems and methods can also be practiced in distributed computing environments, where tasks or sets of instructions are performed or executed by remote processing devices, which are linked through a communications network. In a distributed computing environment computer- or processor-readable instructions (also referred to in the present application as program modules), application programs and/or data, may be stored in both local and remote memory storage devices (e.g., non-transitory computer- or processor-readable media). Digital computer 102 may include at least one digital processor 106, at least one system memory 108, and at least one system bus 110 that provides communicative coupling between various system components, for example between system memory 108 and digital processor(s) 106.

Digital processor(s) 106 may be any logic processing unit, for example with one or more cores, for instance one or more central processing units ("CPUs"), graphics processing units ("GPUs"), digital signal processors ("DSPs"), application-specific integrated circuits ("ASICs"), field-programmable gate arrays ("FPGAs"), etc.

Unless described otherwise, the construction and operation of the various blocks shown in FIG. 1 are of conventional design. As a result, such blocks need not be described in further detail herein, as they will be understood by those skilled in the relevant art.

Digital computer 102 may include a user input/output subsystem 112. In some implementations, the user input/output subsystem includes one or more user input/output components such as a display 114, mouse 116, and/or keyboard 118. System bus 110 can employ any known bus structures or architectures, including a memory bus with a memory controller, a peripheral bus, and a local bus. System memory 108 may include non-volatile memory, such as read-only memory ("ROM"), static random-access memory ("SRAM"), Flash NAND; and volatile memory such as random-access memory ("RAM") (not shown), all of which are examples of non-transitory computer- or processor-readable media.

A basic input/output system ("BIOS") 120, which can form part of the ROM, contains basic routines that help transfer information between elements within digital computer 102, such as during startup.

Digital computer 102 may also include other non-volatile memory 122. Non-volatile memory 122 may take a variety of forms, including: a hard disk drive for reading from and writing to a hard disk, an optical disk drive for reading from and writing to removable optical disks, and/or a magnetic disk drive for reading from and writing to magnetic disks, all of which are examples of non-transitory computer- or processor-readable media. The optical disk can be a CD-ROM or DVD, while the magnetic disk can be a magnetic floppy disk or diskette. Non-volatile memory 122 may communicate with digital processor via system bus 110 and may include appropriate interfaces or controllers 124 coupled to system bus 110. Non-volatile memory 122 may serve as long-term storage for computer- or processor-readable instructions, data structures, or other data (also called program modules) for digital computer 102.

Although digital computer 102 has been described as employing hard disks, optical disks and/or magnetic disks, those skilled in the relevant art will appreciate that other types of non-volatile computer-readable media may be employed, such magnetic cassettes, flash memory cards, Flash, ROMs, smart cards, etc., all of which are further examples of non-transitory computer- or processor-readable media. Those skilled in the relevant art will appreciate that some computer architectures conflate volatile memory and non-volatile memory. For example, data in volatile memory can be cached to non-volatile memory. Or a solid-state disk that employs integrated circuits to provide non-volatile memory. Some computers place data traditionally stored on disk in memory. As well, some media that are traditionally regarded as volatile can have a non-volatile form, e.g., Non-Volatile Dual In-line Memory Module variation of Dual In-Line Memory Modules.

Various sets of computer-readable or processor-readable instructions (also referred to in the present application as program modules), application programs and/or data can be stored in system memory 108. For example, system memory 108 may store an operating system 126, and a set of computer- or processor-readable server instructions (i.e., server modules) 128. In some implementations, server module 128 includes instructions for communicating with remote clients and scheduling use of resources including resources on the digital computer 102 and analog computer 104. For example, a Web server application and/or Web client or browser application for permitting digital computer 102 to exchange data with sources via the Internet, corporate Intranets, or other networks, as well as with other server applications executing on server computers.

In some implementations, system memory 108 may store other sets of computer-readable or processor-readable instructions 130 such as calculation instructions, analog computer interface instructions and the like.

While shown in FIG. 1 as being stored in system memory 108, server instructions 128, other instructions 130, and other data (not shown in FIG. 1) can also be stored elsewhere including in non-volatile memory 122 or one or more other non-transitory computer-readable or processor-readable media.

The analog computer 104 can be provided in an isolated environment (not shown in FIG. 1). For example, where analog computer 104 is a quantum computer, the environment shields the internal elements of the quantum computer from heat, magnetic field, and the like, and other external noise (not shown in FIG. 1) and/or which cools the analog processor to temperatures (i.e., critical temperature) at or below which the circuitry of analog processor 104 becomes superconductive. In contrast, the digital computer 102 will typically operate at much higher temperatures (e.g., room temperature) at which superconductivity does not occur and/or may employ materials that are not superconductive even at or below the critical temperature. Analog computer 104 includes an analog processor 132. Examples of analog processor 132 include quantum processors such as those described below with reference to FIG. 2.

A quantum processor includes programmable elements such as qubits, couplers, and other devices. The qubits can be read out via readout system 134. The readouts can be fed to various sets of computer-readable or processor-readable instructions for digital computer 102, including server module 128, or other modules 130 stored in non-volatile memory 122, returned over a network or the like. The qubits can be controlled via qubit control system 136. The couplers can be controlled via coupler control system 138. In some implementations, qubit control system 136 and coupler control system 138 are used to implement quantum annealing on analog processor 132, as described in the present application.

Figure 2:
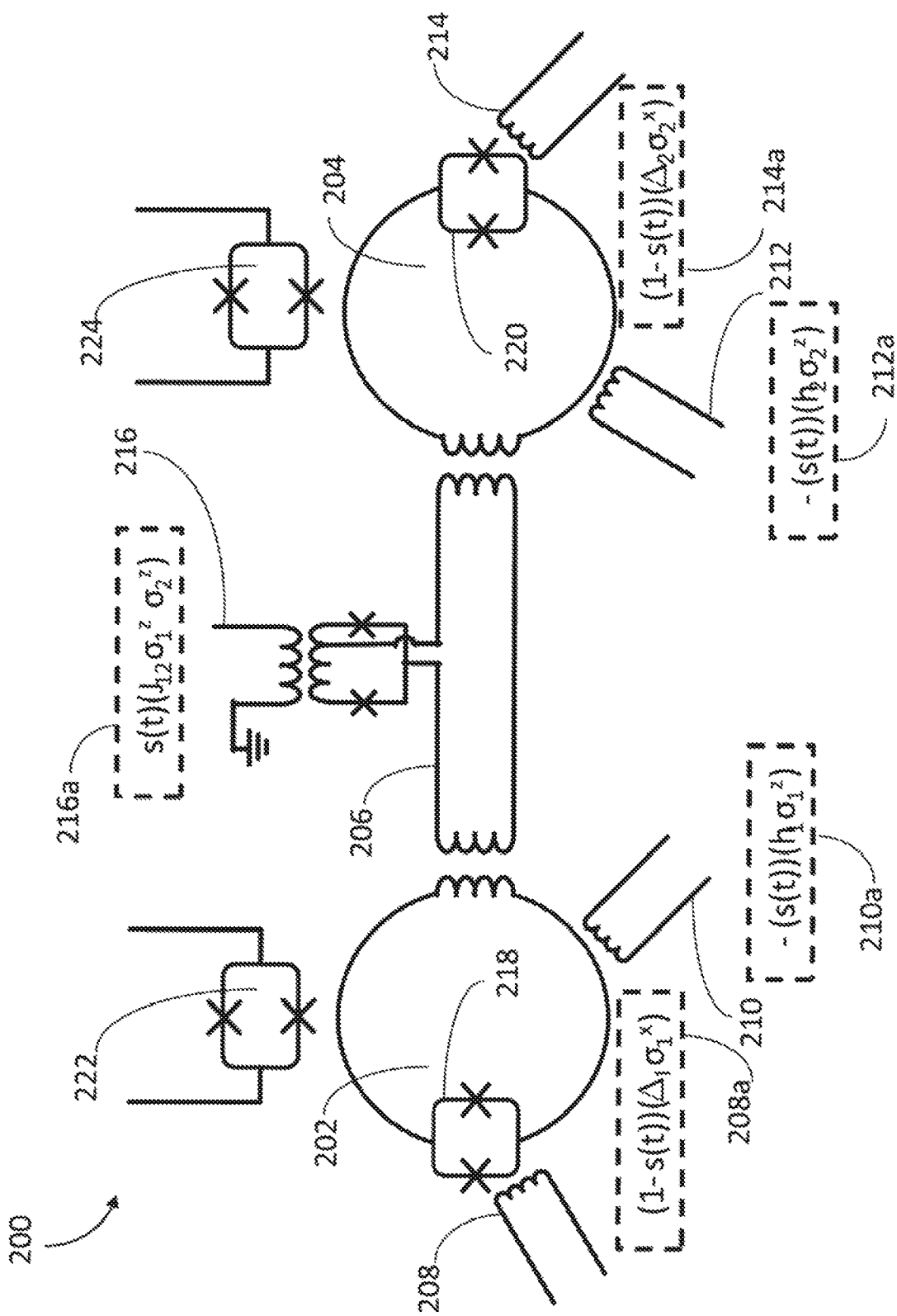
FIG. 2 is a schematic diagram of a portion of an exemplary superconducting quantum processor designed for quantum annealing (and/or adiabatic quantum computing) components from which may be used to implement the present systems and devices, in accordance with the present systems, devices, articles, and methods.

In some implementations, digital computer 102 can operate in a networking environment using logical connections to at least one client computer system. In some implementations, digital computer 102 is coupled via logical connections to at least one database system. These logical connections may be formed using any means of digital communication, for example, through a network, such as a local area network ("LAN") or a wide area network ("WAN") including, for example, the Internet. The networking environment may include wired or wireless enterprise-wide computer networks, intranets, extranets, and/or the Internet. Other embodiments may include other types of communication networks such as telecommunications networks, cellular networks, paging networks, and other mobile networks. The information sent or received via the logical connections may or may not be encrypted. When used in a LAN networking environment, digital computer 102 may be connected to the LAN through an adapter or network interface card ("NIC") (communicatively linked to system bus 110). When used in a WAN networking environment, digital computer 102 may include an interface and modem (not shown), or a device such as NIC, for establishing communications over the WAN. Non-networked communications may additionally, or alternatively, be employed.
Exemplary superconducting Quantum Processor for Quantum Annealing FIG. 2 is a schematic diagram of a portion of an exemplary superconducting quantum processor 200 designed for quantum annealing (and/or adiabatic quantum computing) components from which may be used to implement the present systems and devices. The portion of superconducting quantum processor 200 shown in FIG. 2 includes two superconducting qubits 202, and 204. Also shown is a tunable coupling (diagonal coupling) via coupler 206 between qubits 202 and 204 (i.e., providing 2-local interaction). While the portion of quantum processor 200 shown in FIG. 2 includes only two qubits 202, 204 and one coupler 206, those of skill in the art will appreciate that quantum processor 200 may include any number of qubits and any number of couplers coupling information between them.

The portion of quantum processor 200 shown in FIG. 2 may be implemented to physically realize quantum annealing and/or adiabatic quantum computing. Quantum processor 200 includes a plurality of interfaces 208-216 that are used to configure and control the state of quantum processor 200. Each of interfaces 208-216 may be realized by a respective inductive coupling structure, as illustrated, as part of a programming subsystem and/or an evolution subsystem. Such a programming subsystem and/or evolution subsystem may be separate from quantum processor 200, or it may be included locally (i.e., on-chip with quantum processor 200).

In the operation of quantum processor 200, interfaces 208 and 212 may each be used to couple a flux signal into a respective compound Josephson junction 218 and 220 of qubits 202 and 204, thereby realizing a tunable tunneling term (the $\Delta_i$ term) in the system Hamiltonian. This coupling provides the off-diagonal $\sigma^x$ terms of the Hamiltonian and these flux signals are examples of "delocalization signals".

In some implementations, the tunneling term is selected to make a first portion of the qubits on the quantum processor more classical relative a second portion of the qubits. For example, qubit 202 may be a hidden unit in a Boltzmann machine and have a smaller tunneling term relative to qubit 204.

Similarly, interfaces 210 and 212 may each be used to apply a flux signal into a respective qubit loop of qubits 202 and 204, thereby realizing the $h_i$ terms in the system Hamiltonian. This coupling provides the diagonal $\sigma^z$ terms in the system Hamiltonian. Furthermore, interface 216 may be used to couple a flux signal into coupler 206, thereby realizing the $J_{ij}$ term(s) in the system Hamiltonian. This coupling provides the diagonal $\sigma_i^z \sigma_j^z$ terms in the system Hamiltonian.

In FIG. 2, the contribution of each of interfaces 208-216 to the system Hamiltonian is indicated in boxes 208a-216a, respectively. As shown, in the example of FIG. 2, the boxes 208a-216a are elements of time-varying Hamiltonians for quantum annealing and/or adiabatic quantum computing.

Throughout this specification and the appended claims, the term "quantum processor" is used to generally describe a collection of physical qubits (e.g., qubits 202 and 204) and couplers (e.g., coupler 206). The physical qubits 202 and 204 and the coupler 206 are referred to as the "programmable elements" of the quantum processor 200 and their corresponding parameters (e.g., the qubit $h_i$ values and the coupler $J_{ij}$ values) are referred to as the "programmable parameters" of the quantum processor. In the context of a quantum processor, the term "programming subsystem" is used to generally describe the interfaces (e.g., "programming interfaces" 210, 212, and 216) used to apply the programmable parameters to the programmable elements of the quantum processor 200 and other associated control circuitry and/or instructions.

As previously described, the programming interfaces of the programming subsystem may communicate with other subsystems which may be separate from the quantum processor or may be included locally on the processor. As described in more detail later, the programming subsystem may be configured to receive programming instructions in a machine language of the quantum processor and execute the programming instructions to program the programmable elements in accordance with the programming instructions. Similarly, in the context of a quantum processor, the term "evolution subsystem" generally includes the interfaces (e.g., "evolution interfaces" 208 and 214) used to evolve the programmable elements of the quantum processor 200 and other associated control circuitry and/or instructions. For example, the evolution subsystem may include annealing signal lines and their corresponding interfaces (208, 214) to the qubits (202, 204).

Quantum processor 200 also includes readout devices 222 and 224, where readout device 222 is associated with qubit 202 and readout device 224 is associated with qubit 204. In some embodiments, such as shown in FIG. 2, each of readout devices 222 and 224 includes a DC-SQUID inductively coupled to the corresponding qubit. In the context of quantum processor 200, the term "readout subsystem" is used to generally describe the readout devices 222, 224 used to read out the final states of the qubits (e.g., qubits 202 and 204) in the quantum processor to produce a bit string. The readout subsystem may also include other elements, such as routing circuitry (e.g., latching elements, a shift register, or a multiplexer circuit) and/or may be arranged in alternative configurations (e.g., an XY-addressable array, an XYZ-addressable array, etc.). Qubit readout may also be performed using alternative circuits, such as that described in PCT Patent Publication WO2012064974.

While FIG. 2 illustrates only two physical qubits 202, 204, one coupler 206, and two readout devices 222, 224, a quantum processor (e.g., processor 200) may employ any number of qubits, couplers, and/or readout devices, including a larger number (e.g., hundreds, thousands or more) of qubits, couplers and/or readout devices. The application of the teachings herein to processors with a different (e.g., larger) number of computational components should be clear to those of ordinary skill in the art.

Examples of superconducting qubits include superconducting flux qubits, superconducting charge qubits, and the like. In a superconducting flux qubit, the Josephson energy dominates or is equal to the charging energy. In a charge qubit it is the reverse. Examples of flux qubits that may be used include RF-SQUIDs, which include a superconducting loop interrupted by one Josephson junction, persistent current qubits, which include a superconducting loop interrupted by three Josephson junctions, and the like.

The qubits and coupling devices in a quantum processor may be arranged according to an architecture into a topology such that a certain number of qubits may be laid out in a sub-topology of qubits (hereinafter, "sub-topology"). A sub-topology is a portion of a quantum processor topology comprising qubits and coupling devices. A plurality of sub-topologies may be repeated or tiled (or otherwise directly communicatively coupled to one another) over an area of a quantum processor to produce a certain quantum processor topology.

In some implementations, each sub-topology in a topology is identical to each other sub-topology in the same topology. In other implementations, one or more sub-topologies in the topology comprise a different configuration of qubits and coupling devices than another sub-topology in the same topology.

Calibration of an Analog Processor

An analog processor can be calibrated to provide a desired level of performance on one or more types of problems. Conventionally, an analog processor is calibrated to provide a desired level of performance on a broad variety of problems.

For some applications, it can be desirable for the devices of an analog processor to be behave uniformly. The analog processor can be a quantum processor. For example, for some applications, it can be desirable for qubits, qubit chains, couplers between qubits, and couplers between qubit chains of the quantum processor to exhibit uniform behavior.

In one implementation, a graph is embedded on an analog processor, and devices in the analog processor are expected to exhibit uniform behavior, through an automorphism of the graph. An automorphism may result from a structure of the analog processor, for example from a symmetry of the analog processor, or from a symmetry of devices in the analog processor.

In another implementation, different embeddings of the problem on an analog processor are used, and the embeddings are expected to exhibit uniform behavior (i.e., have the same or at least similar statistics), through an automorphism of the graph. An automorphism may result from a structure of the analog processor, for example from a symmetry of the analog processor, or from a symmetry of devices in the analog processor.

In yet another implementation, a graph can be embedded on one physical instance of a quantum processor, and an automorphism of the graph can be embedded on another physical instance of the quantum processor. Since the physical instances are logically equivalent to each other, through the automorphism, the physical instances can be expected to exhibit the same behavior as each another.

In yet another implementation, a graph is embedded multiple times on a quantum processor with different embeddings. Through automorphism of the embedded graphs, statistics between embeddings can be expected to exhibit at least similar characteristics.

Chimera Topology Example

The systems and methods described in the present application can be used to improve calibration and/or performance of an analog processor where devices in the analog processor are expected individually and/or collectively to exhibit uniform behavior. One reason for expecting uniform behavior can be the structure of the analog processor, for example the topology of the analog processor, and, in some examples, symmetries in the topology of the analog processor.

Figure 3:
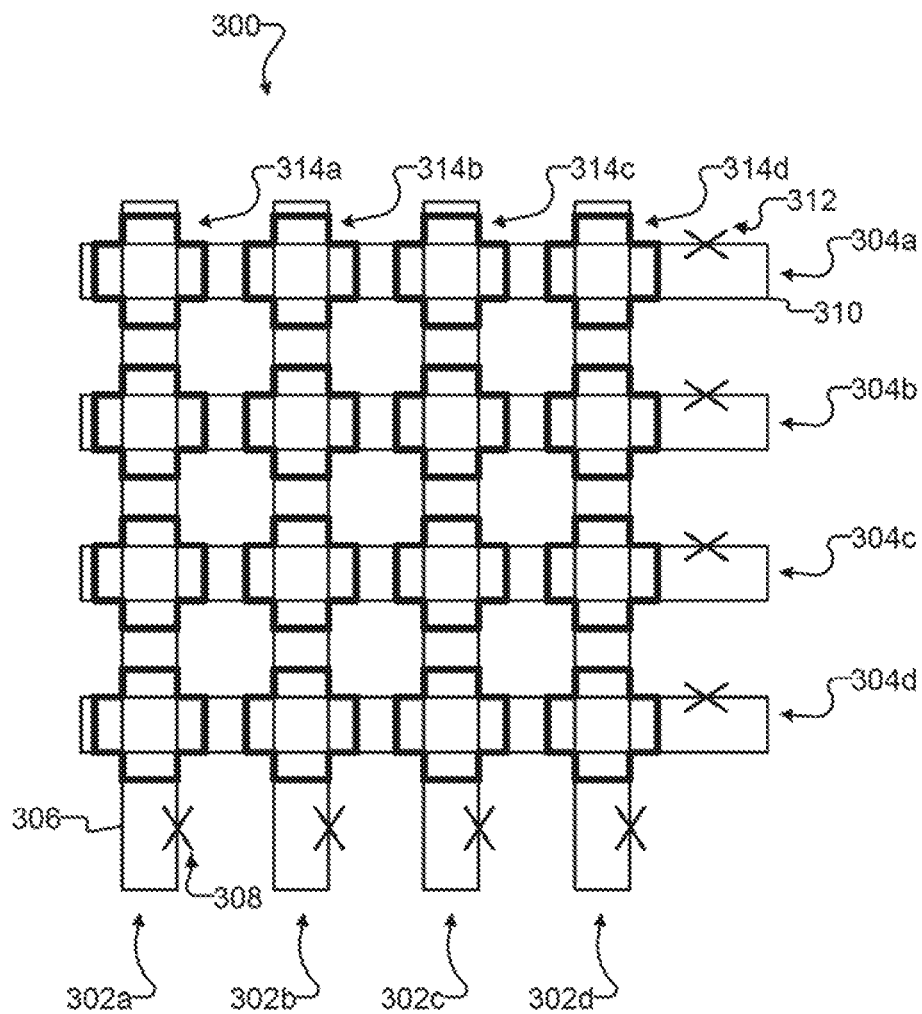
FIG. 3 is a schematic diagram illustrating an example implementation of a cell of a quantum processor (such as the quantum processor of FIG. 1), in accordance with the present systems, devices, articles, and methods.

The Chimera topology, described below with reference to FIG. 3, is an example of a topology of an analog processor. The Chimera topology is an example of a topology with automorphisms. The systems and methods described in the present application can, for example, be used to improve calibration and/or performance of a quantum processor having a Chimera topology.

FIG. 3 is a schematic diagram illustrating an example implementation of a cell 300 of a quantum processor (such as quantum processor 132 of FIG. 1), in accordance with the present systems, devices, articles, and methods. Cell 300 includes qubits 302a, 302b, 302c, and 302d (collectively 302) and qubits 304a, 304b, 304c, and 304d (collectively 304). Qubits 302 are laid out vertically in FIG. 3, and qubits 304 are laid out horizontally in FIG. 3. A person of skill in the art will appreciate that while four qubits are illustrated both horizontally and vertically, this number is for example only, and other implementations may comprise more than four qubits or less than four qubits.

Qubits 302 and 304 may be superconducting qubits. Each qubit of qubits 302 may include a respective loop of superconducting material 306 (only one called out in FIG. 3) interrupted by at least one respective Josephson junction 308 (only one called out in FIG. 3). Each qubit of qubits 304 may include a respective loop of superconducting material 310 (only one called out in FIG. 3) interrupted by at least one respective Josephson junction 312 (only one called out in FIG. 3).

Couplers 314a, 314b, 314c, and 314d (collectively 314, only four called out in FIG. 3) can provide communicative coupling between qubits 302 and 304. Each qubit of qubits 302 can be coupled to each qubit of qubits 304 through four respective couplers from couplers 314 in a region proximate to where a portion of each qubit of qubits 302 crosses a portion of a qubit of qubits 304. Each coupler of couplers 314 may be a respective loop of superconducting material wherein the loop or superconducting material may define a perimeter to a coupling region. Each coupler of couplers 314 may be a respective loop of superconducting material interrupted by at least one respective Josephson junction wherein the loop or superconducting material may define a perimeter to a coupling region wherein coupling occurs along the perimeter by having a current-carrying wire, such as loop of superconducting material (e.g., loop 306 of qubit 302a or loop 310 of qubit 304a) run parallel in some manner to a coupler of couplers 314 to allow flux from current within the loop of superconducting material to induce a current to flow in a coupler of couplers 314 and vice versa. Couplers 314 may be tunable in that the communicative coupling provided by couplers 314 between two respective qubits of qubits 302 and 304 can be changed during the operation of an analog processor. The coupling may change during computation. The coupling may change between computations to embed a problem into the analog processor. The coupling may be expressed as a coupling strength.

Figure 4:
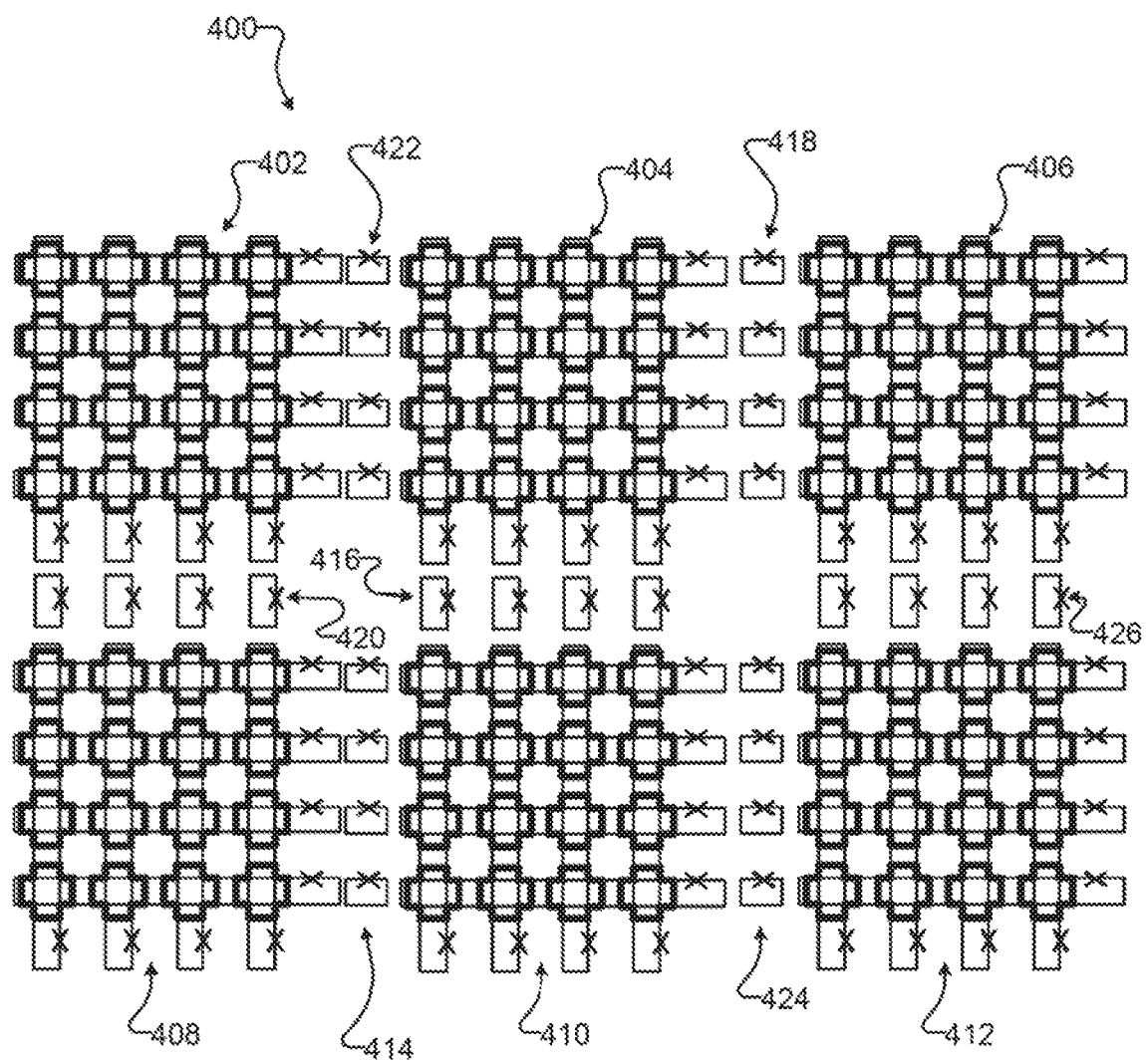
FIG. 4 is a schematic diagram illustrating an example implementation of a topology of a quantum processor (such as the quantum processor of FIG. 1), in accordance with the present systems, devices, articles, and methods.

FIG. 4 is a schematic diagram illustrating an example implementation of a topology 400 of a quantum processor (such as quantum processor 132 of FIG. 1), in accordance with the present systems, devices, articles, and methods. Topology 400 comprises sub-topologies 402, 404, 406, 408, 410, and 412. Couplers 414, 416, 418, 420, 422, 424, and 426 providing communicative coupling between sub-topologies may also be located within topology 400. Sub-topologies 408 and 404 can be communicatively coupled to sub-topologies 410 and 406 through couplers 414, 416, and 418 such that a 2×$K_8$ graph can be embedded into topology 400. Each $K_8$ graph, or portion thereof, may be coupled to variables from another $K_8$ graph. For example, one $K_8$ graph may be embedded into sub-topologies 402, 404, and 408 and another $K_8$ graph may be embedded into sub-topologies 406, 410, 412. Couplers 414, 416, 418, 420, 422, 424, and 426 may be controllable such that both ferromagnetic couplings, anti-ferromagnetic couplings, zero couplings and transverse couplings may be created between pairs of adjacent qubits.

In an example implementation, a graph has a Chimera topology (see Glossary) with a Chimera cell in which a coupling strength $J_{ij}=1$ for all qubit pairs $\{i,j\}$, and a flux bias $h_i=0$ for all qubits $\{i\}$. The graph is edge-transitive (see Glossary). There is a permutation of qubits that maps a pair of coupled qubits {i,j} to another pair of coupled qubits {k,l}.

Ideally, both couplers should be frustrated with the same probability (see Glossary for a definition of frustration). If one coupler is frustrated less than the other, then the coupling strength of at least one of the two couplers can be adjusted to improve the degree of homogeneity of the statistics of frustration.

Since the flux bias is set to zero, the expected average spin for each qubit should be zero. If an average spin is greater than or less than zero by more than a predetermined threshold, then a flux bias offset can be applied to the qubit to cause the average spin to be within the predetermined threshold from zero or at least closer to zero than without the flux bias offset.

In an example scenario of simulation of a repeating lattice (for example a square lattice or a triangular lattice), ideally the logical qubits and the logical couplers should behave in the same way. In practice, for a given set of calibration parameters for the quantum processor, systematic errors can be observed, and the systematic errors can interact with each other in a chaotic manner. The present application describes systems and methods for refining a calibration to improve the degree of homogeneity of the statistics of frustration for the logical couplers, and to cause the average net magnetization of the logical qubits (also referred to in the present application as qubit chains) to be closer to the expected value of zero.

Embedded Triangular Lattice

In an example implementation, the repeating lattice is a triangular lattice. For the triangular lattice, the probability a given coupler is frustrated (at a low temperature) ideally has a value of one-third, and the magnetization of a given qubit ideally has a value zero. At a low temperature, the system can be in a ground state or a state that is close to the ground state. At a low temperature, a solution can be a low-energy solution. A low-energy solution is less likely to be observed at a higher temperature.

In the example implementation, the systems and methods described in the present application for refining the calibration of the quantum processor are implemented using one or more iterations, each iteration including an adjustment of a coupling strength $J_{ij}$, a local bias $h_i$ and/or a flux bias offset to improve the degree of homogeneity of the statistics of frustration. A local bias value can vary as a function of progress through an anneal. A flux bias offset can be applied as a constant value.

Figure 5A:
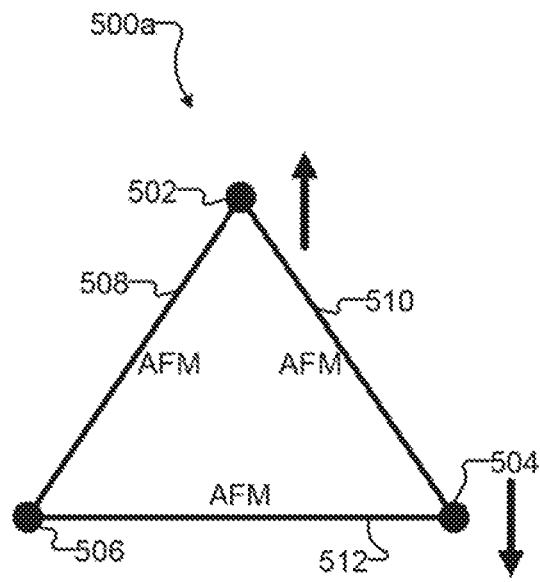
FIG. 5A is a schematic diagram illustrating a portion of an example triangular lattice, in accordance with the present systems, devices, articles, and methods.

FIG. 5A is a schematic diagram illustrating a portion 500a of an example triangular lattice, in accordance with the present systems, devices, articles, and methods. Portion 500a comprises three vertices 502, 504, and 506, and three edges 508, 510, and 512. In one implementation of an analog processor to which portion 500a belongs, vertices 502, 504, and 506 are qubits, and edges 508, 510, and 512 are couplers.

Figure 5B:
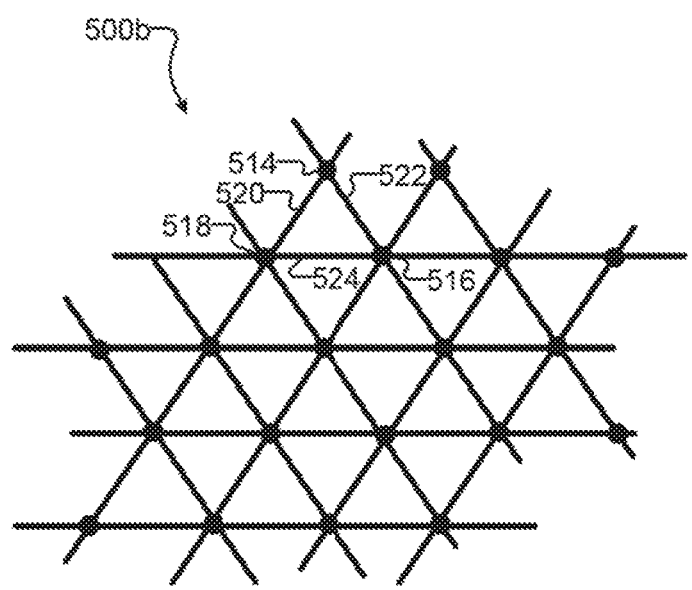
FIG. 5B is a schematic diagram illustrating an extended portion of an example triangular lattice, in accordance with the present systems, devices, articles, and methods.

FIG. 5B is a schematic diagram illustrating an extended portion 500b of an example triangular lattice, in accordance with the present systems, devices, articles, and methods. Extended portion 500b comprises vertices 514, 516, and 518, and edges 520, 522, and 524 (for clarity, only three vertices and three edges called out in FIG. 5B).

A triangular lattice can have one or more symmetries. For example, each triangle in the lattice can have exactly one frustrated edge (in a low energy solution), and, except for triangles subject to non-periodic boundary conditions, the three edges of the triangle can be equivalent to each other by rotation.

Referring to FIG. 5A, the triangle formed by vertices 502, 504, and 506, and edges 508, 510, and 512 can have exactly one frustrated edge, and (provided the triangle is not subject to non-periodic boundary conditions) edges 508, 510, and 512 can be equivalent to each other by rotation.

In one implementation, vertices 502, 504, and 506 are qubits in a quantum processor, and can be associated with a spin vector. In the example illustrated in FIG. 5A, vertex 502 has spin "up", and vertex 504 has spin "down". In the same implementation, edges 508, 510, and 512 are couplers, each with anti-ferromagnetic (AFM) coupling. In the illustrated example of FIG. 5A, the spin of vertex 506 is indeterminate, i.e., cannot be selected to satisfy the constraints imposed by the spins of 502 and 504, and the AFM coupling of 508, 510, and 512.

In another implementation, a lattice can be a torus or a half-torus. The half-torus can be opened to form a cylinder. The toroidal or half-toroidal lattice can be a topology of an analog processor such as a quantum processor. The lattice can include couplers with rotational symmetry, and is an example of a topology with automorphisms. The systems and methods described in the present application can, for example, be used to improve calibration and/or performance of a quantum processor having a toroidal or half-toroidal topology.

In another implementation, adjustments can be made to anneal offsets. In an example implementation of a quantum processor, one subset of qubits can have different tunneling characteristics to another subset of qubits. In this example, it can be beneficial to include adjustments to anneal offsets to at least improve and/or homogenize statistics. For example, the quantum processor can include an integrated circuit with horizontally-oriented qubits and vertically-oriented qubits, the horizontally-oriented qubits having different tunneling characteristics from the vertically-oriented qubits. Anneal offsets can be adjusted using the systems and methods described in the present application to at least improve and/or homogenize statistics.

In other implementations, at least one other suitable parameter can be adjusted and/or applied to improve and/or homogenize statistics.

In yet another implementation, the processor is first run with only the chain couplings active, using flux offsets to balance the chains to degeneracy. The processor is then run with the problem Hamiltonian, and adjustments made to flux bias offsets and/or coupling strengths in accordance with the systems and methods described in the present application.

In one implementation, the systems and methods described in the present application can be used to improve or refine a calibration in which two devices are expected to behave at least approximately identically.

In an example implementation, the calibration can be refined using an iterative method. The following acts are iterated until an exit criterion is reached.

First, a computational problem is run on an analog processor such as a quantum processor. The computational problem can be embedded on the analog processor, and can be run repeatedly multiple times. It can be beneficial for the multiple runs to be independent of each other. In some implementations, it can be beneficial to allow sufficient time to elapse between each run, for example, to at least reduce dependencies or correlations between runs. In one implementation, it can be beneficial to allow sufficient time to elapse between runs to allow at least a degree of spin-bath depolarization to occur.

A processor (e.g., hardware circuitry) next determines magnetizations and correlations for logical qubits and logical couplers. The expected (ideal) values are zero and minus one-third (−⅓), respectively. The processor then computes and applies one or more flux bias offsets and/or one or more coupling strengths. A flux bias offset adjustment can be calculated to cause a magnetization to be zero. A coupling strength adjustment can be calculated to cause a correlation to be −⅓.

Figure 6:
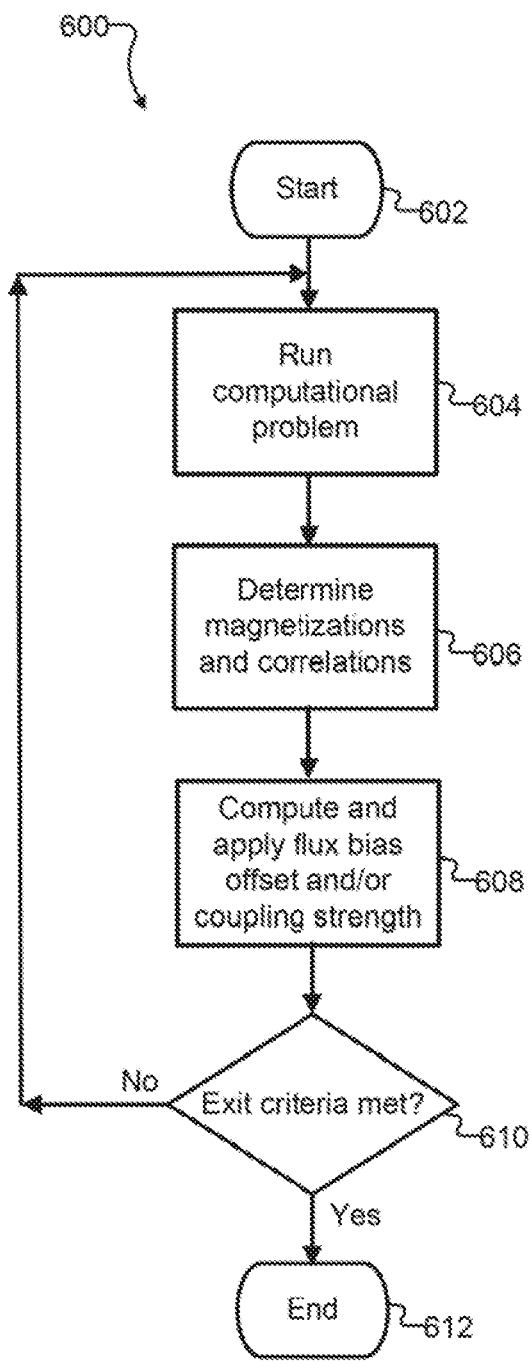
FIG. 6 is a flow chart illustrating an example implementation of a method of operation of an analog processor, in accordance with the present systems, devices, articles, and methods.

FIG. 6 is a flow chart illustrating an example implementation of a method 600 of operation of an analog processor, in accordance with the present systems, devices, articles, and methods. Method 600 of FIG. 6 comprises a plurality of acts. One or more of these acts may be performed by (or via) one or more circuits, for instance one or more processors, e.g., digital processors, and analog processors such as quantum processors, or a hybrid computer (for example hybrid computer 100 of FIG. 1) that includes both digital and analog processors. For the purposes of the description of FIG. 6, the acts are assumed to be performed by a hybrid computer comprising a quantum processor. Those of skill in the art will appreciate that alternative implementations may omit certain acts and/or include additional acts.

Method 600 starts at 602, for example in response to submission of a computational problem or in response to an invocation by another method. At 604, the digital processor of the hybrid computer sends a computational problem to the analog processor to be run, the hybrid computer embeds the computational problem on the analog processor to generate an embedded problem, runs the embedded problem on the analog processor, and returns the results to the digital processor. The problem can be run repeatedly on the analog processor multiple times. The number of runs can be between ten (10) and ten thousand (10,000). The number of runs can be selected to cause systematic biases to be detectable using statistics of the results.

At 606, the hybrid computer determines one or more statistics of the results. The statistics can include magnetizations and spin-spin correlations, for example.

At 608, the hybrid computer computes and applies values of at least one programmable parameter of the analog processor. The programmable parameters can include local fields, flux bias offsets, coupling strengths, and/or anneal offsets, for example.

At 610, the hybrid computer determines whether an exit criterion has been met. The exit criterion can be a single criterion or a combination of more than one criterion. Example criteria can include thresholds based on a number of iterations performed by the hybrid computer, a magnitude of a deviation of the statistics from expected statistics, a degree of improvement in the homogeneity of the statistics, a rate of convergence, and/or an execution time for method 600.

In response to determining an exit criterion has been met (YES) at 610, method 600 ends at 612. In response to determining an exit criterion has not been met (NO) at 610, control of method 600 returns to 604 where method 600 begins a further iteration of acts 604, 606, 608, and 610.

Statistics can include first-order statistics such as the magnetization or average magnetization. Statistics can include second-order statistics such as spin-spin correlations of coupled pairs of qubits. Statistics can include higher-order statistics such as higher-order effects between devices. For example, statistics can include the degree of spin-spin correlation between one or more sets of three qubits arranged in a triangular lattice. Statistics can include other suitable statistical measures.

In one implementation, an adjustment to a flux bias offset can be at least approximately proportional to a measured deviation of the magnetization from its expected value. An adjustment to a coupling strength can be at least approximately proportional to a measured deviation of the correlation from its expected value.

In one implementation, the flux bias offset adjustment and/or the coupling strength adjustment is sufficiently small to avoid overcompensation and/or ringing effects.

In one implementation, the number of iterations (the number of times method 600 performs acts 604, 606, 608, and 610) is approximately ten (10).

In one implementation, a damping parameter is included in the method described above. A benefit of the damping parameter is improved stability and/or performance of the method, for example in reducing ringing effects and/or reducing the number of iterations needed to achieve a desired outcome. A damping parameter can be used to control the size of adjustments to a flux bias offset and/or a coupling strength during each iteration.

The exit criterion can be one of the following or another exit criterion or a combination of criteria: a) when the number of iterations equals a predetermined maximum number of iterations, b) when the time equals or exceeds a predetermined time limit, c) when a magnitude of a measured deviation from the expected (ideal or nominal) value is less than a predetermined threshold, d) when the improvement in the homogeneity of the statistics is less than a predetermined threshold, e) when the rate of convergence in the improvement in the homogeneity of the statistics is less than a predetermined threshold, and/or f) another suitable criterion.

A refinement of the calibration in accordance with the systems and methods described in the present application can be performed as needed. In some implementations, the refinement is typically stable and may persist over time. An occasional adjustment (also referred to in the present application as a shim) may be needed to improve the statistics.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other analog processors, not necessarily the exemplary quantum processors generally described above.

The various embodiments described above can be combined to provide further embodiments. To the extent that they are not inconsistent with the specific teachings and definitions herein, all of the US patent application publications, US patent applications, U.S. patents, International patent applications, foreign patents, and foreign patent applications referred to in this specification and/or listed in the Application Data Sheet that are commonly assigned to D-Wave Systems Inc. are incorporated herein by reference, in their entirety, including but not limited to: U.S. Pat. Nos. 7,984,012; 8,244,662; 8,174,305; PCT Patent Publication WO2012064974; US Patent Application Publication No. US2015/0032994; PCT Patent Application Publication No. WO2017075246; US Patent Application Publication No. 2015/363708; U.S. patent application Ser. No. 15/448,361;

and U.S. Provisional Patent Application No. 62/620,282. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of operation of a hybrid computing system that comprises an analog processor and at least one digital processor, the analog processor and the at least one digital processor communicatively coupled to one another, the analog processor comprising a plurality of analog devices, the plurality of analog devices characterized by values of at least one programmable parameter, the at least one programmable parameter programmable by the at least one digital processor, the method comprising:
embedding, by the at least one digital processor, a computational problem on the analog processor to generate an embedded problem having one or more symmetries;
causing, by the at least one digital processor, a first repeated running of the embedded problem on the analog processor to generate a first plurality of candidate solutions to the computational problem;
receiving, by the at least one digital processor, the first plurality of candidate solutions to the computational problem;
determining, by the at least one digital processor, a value for at least one statistical feature of the first plurality of candidate solutions to the computational problem;
adjusting, by the at least one digital processor, the values of the at least one programmable parameter of the plurality of analog devices in the analog processor to at least partially compensate for deviations from an expected value of the at least one statistical feature, the expected value of the at least one statistical feature inferred from the one or more symmetries of the embedded problem; and
causing, by the at least one digital processor, a second repeated running of the embedded problem on the analog processor to generate a second plurality of candidate solutions to the computational problem.

2. The method of claim 1, wherein embedding, by the at least one digital processor, a computational problem on the analog processor to generate an embedded problem includes embedding, by the at least one digital processor, a computational problem on a quantum processor.

3. The method of claim 2, wherein embedding, by the at least one digital processor, a computational problem on a quantum processor includes embedding, by the at least one digital processor, a computational problem on a superconducting quantum processor.

4. The method of claim 3, wherein adjusting the values of the at least one programmable parameter of the plurality of analog devices in the analog processor to at least partially compensate for deviations from an expected value of the at least one statistical feature includes adjusting the values of the at least one programmable parameter of a plurality of superconducting flux qubits and superconducting coupling devices in the superconducting quantum processor.

5. The method of claim 4, wherein adjusting the values of the at least one programmable parameter of a plurality of superconducting flux qubits and superconducting coupling devices in the superconducting quantum processor includes adjusting values of at least one of a flux, a flux bias offset, a coupling strength, and an anneal offset.

6. The method of claim 1, wherein embedding, by the at least one digital processor, a computational problem on the analog processor to generate an embedded problem includes embedding, by the at least one digital processor, an optimization problem on the analog processor.

7. The method of claim 1, wherein adjusting values of the at least one programmable parameter of the plurality of analog devices in the analog processor to at least partially compensate for deviations from an expected value of the at least one statistical feature, the expected value of the at least one statistical feature inferred from the structure of the embedded problem includes adjusting the at least one programmable parameter of the plurality of analog devices in the analog processor to at least partially compensate for deviations from an expected value of the at least one statistical feature, the expected value of the at least one statistical feature inferred from one or more graph automorphisms of the embedded problem.

8. The method of claim 1, wherein determining, by the at least one digital processor, a value for at least one statistical feature of the first plurality of candidate solutions to the computational problem includes determining, by the at least one digital processor, a value for at least one of a magnetization and a spin-spin correlation.

9. The method of claim 1, wherein embedding, by the at least one digital processor, a computational problem on the analog processor to generate an embedded problem includes embedding, by the at least one digital processor, a computational problem on a topology comprising a repeating lattice.

10. The method of claim 9, wherein embedding, by the at least one digital processor, a computational problem on a topology comprising a repeating lattice includes embedding, by the at least one digital processor, a computational problem on a topology comprising at least one of a triangular lattice and a square lattice.

11. The method of claim 1, further comprising:
receiving, by the at least one digital processor, the second plurality of candidate solutions to the computational problem;
determining, by the at least one digital processor, a value for at least one statistical feature of the second plurality of candidate solutions to the computational problem;
adjusting, by the at least one digital processor, values of the at least one programmable parameter of the plurality of analog devices in the analog processor to at least partially compensate for deviations from the expected value of the at least one statistical feature; and
causing, by the at least one digital processor, a third repeated running of the embedded problem on the analog processor to generate a third plurality of candidate solutions to the computational problem.

12. A hybrid computing system, comprising:
an analog processor comprising a plurality of analog devices;
at least one digital processor communicatively coupled to the at least one analog processor; and
at least one non-transitory computer-readable storage medium that stores processor-executable instructions, which when executed causes the at least one digital processor to:

embed a computational problem on the analog processor to generate an embedded problem having one or more symmetries;

cause a first repeated running of the embedded problem on the analog processor to generate a first plurality of candidate solutions to the computational problem;

receive the first plurality of candidate solutions to the computational problem;

determine a value for at least one statistical feature of the first plurality of candidate solutions to the computational problem;

adjust values of at least one programmable parameter of the plurality of analog devices in the analog processor to at least partially compensate for deviations from an expected value of the at least one statistical feature, the expected value of the at least one statistical feature inferred from the one or more symmetries of the embedded problem; and cause a second repeated running of the embedded problem on the analog processor to generate a second plurality of candidate solutions to the computational problem.

13. The hybrid computing system of claim 12, wherein the analog processor includes a quantum processor.

14. The hybrid computing system of claim 13, wherein the quantum processor includes a superconducting quantum processor.

15. The hybrid computing system of claim 14, wherein the at least one programmable parameter of the plurality of analog devices includes at least one programmable parameter of a plurality of superconducting flux qubits and superconducting coupling devices in the superconducting quantum processor.

16. The hybrid computing system of claim 15, wherein the processor-executable instructions, which when executed causes at least one processor-based device to adjust the values of the at least one programmable parameter of a plurality of superconducting flux qubits and superconducting coupling devices in the superconducting quantum processor include instructions, which when executed causes at least one processor-based device to adjust at least one of a flux, a flux bias offset, a coupling strength and an anneal offset.

17. The hybrid computing system of claim 12, wherein the computational problem includes an optimization problem.

18. The hybrid computing system of claim 12, wherein the structure of the embedded problem includes one or more graph automorphisms of the embedded problem.

19. The hybrid computing system of claim 12, wherein the at least one statistical feature of the first plurality of candidate solutions includes at least one of a magnetization and a spin-spin correlation.

20. The hybrid computing system of claim 12, wherein the analog processor includes a topology comprising a repeating lattice.

21. The hybrid computing system of claim 20, wherein the repeating lattice is at least one of a triangular lattice and a square lattice.

22. The hybrid computing system of claim 12, the at least one non-transitory computer-readable storage medium that stores processor-executable instructions, which when executed further causes the at least one digital processor to:

receive the second plurality of candidate solutions to the computational problem;

determine a value for at least one statistical feature of the second plurality of candidate solutions to the computational problem;

adjust values of the at least one programmable parameter of the plurality of analog devices in the analog processor to at least partially compensate for deviations from the expected value of the at least one statistical feature; and cause a third repeated running of the embedded problem on the analog processor to generate a third plurality of candidate solutions to the computational problem.

* * * * *